United States Patent [19]

Tani

[11] Patent Number: 5,471,297
[45] Date of Patent: Nov. 28, 1995

[54] METHOD OF AND APPARATUS FOR MEASURING OPTICAL DISTORTION

[75] Inventor: Hidehito Tani, Yokohama, Japan

[73] Assignee: Asahi Glass Company Ltd., Tokyo, Japan

[21] Appl. No.: 296,412

[22] Filed: Aug. 26, 1994

[30] Foreign Application Priority Data

Aug. 31, 1993 [JP] Japan ................................. 5-239031

[51] Int. Cl.⁶ .................................................. G01N 21/88
[52] U.S. Cl. .................................................. 356/239
[58] Field of Search ............................... 356/124, 237, 356/239; 348/127, 128, 133

[56] References Cited

U.S. PATENT DOCUMENTS

| | | | |
|---|---|---|---|
| 4,461,570 | 7/1984 | Task et al. | 356/239 |
| 4,647,197 | 3/1987 | Kitaya et al. | 356/239 |
| 4,776,692 | 10/1988 | Kalawsky | 356/239 |

Primary Examiner—F. L. Evans
Attorney, Agent, or Firm—Oblon, Spivak, McClelland, Maier & Neustadt

[57] ABSTRACT

A method of measuring optical distortion of measured material by disposing a background screen (2) having a predetermined regular pattern (3) in rear of a measured material (1) having light transmission properties; disposing an image pick-up device (4) capable of line-scanning in front of the measured material (1); taking a picture of the background screen through the measured material (1) by successively line-scanning the entirety of a range to be measured of the measured material (1) with the image pick-up device (4), and measuring the optical distortion of the measured material (1) on the basis of data in the picture, wherein the regular pattern (3) of the background screen is composed of triangle-wave-like unit patterns (3a), each extending continuously in a predetermined direction, which are arranged at distances of equal pitch.

6 Claims, 7 Drawing Sheets

METHOD OF AND APPARATUS FOR MEASURING OPTICAL DISTORTION

BACKGROUND OF THE INVENTION

1. Field of the Invention

The present invention relates to a method of and an apparatus for measuring a rate of distortion of a measured material having light transmission properties such as a flat glass plate, a curved glass plate or the like. In particular, the present invention relates to an improvement of a method of and an apparatus for measuring optical distortion by measuring a rate of distortion on the basis of light transmitting through a measured material having light transmission properties.

2. Discussion of Background

Generally, when a window glass for an automobile or a building has a large rate of distortion, one sees a distorted outer sight through the window glass. Accordingly, it is necessary that a rate of distortion of window glass sheets should be in a predetermined range by quality control.

Heretofore, as techniques for measuring the distortion of window glass sheets, there are as follows for instance, (1) a regular pattern composed of polka dots is used, and the optical distortion of a measured material is calculated by evaluating the diameters in the longitudinal direction and lateral direction of polka dot data obtained by taking a picture of the measured material such as a window glass sheet, or, (2) a regular pattern composed of a group of points marked by laser beams, for instance, which are arranged at predetermined distances of pitch along the longitudinal direction and the lateral direction, is used, and the optical distortion of a measured material is calculated by detecting a change of distance in coordinates of scattered bright spots of the group of points in a picture taken through the measured material.

As another technique of measuring the distortion of the window glass sheet of this kind, there is a technique disclosed in, for instance, Japanese Unexamined Patent Publication No. 199946/1991. The publication proposes that a screen on which a predetermined bright line is irradiated is disposed in rear of a measured material such as a window glass sheet or the like, and an imaging device such as an ITV camera is disposed in front of the measured material whereby a picture of the bright line is taken through the measured material in the entire region of the measured material with the imaging device, and the optical distortion of the measured material is measured from data in the picture.

However, in the method of evaluating the diameters in the longitudinal direction and the lateral direction of the polka dots, for instance, it is necessary to precisely detect the central position of each of the polka dots in order to correctly obtain the diameters in the longitudinal and lateral directions. Accordingly, the treatment of measuring the optical distortion becomes complicated and it takes much time for the treatment because there are restrictions such as the resolution of the imaging device when the ITV camera is used.

On the other hand, in the method of using the regular pattern composed of a group of points, the optical distortion is obtained on the basis of the distances between points. Accordingly, the data of distances of the points should have a fairly high density in order to measure the optical distortion correctly. However, it is difficult to increase a range to be measured of the measured material when the imaging device is used. On the contrary, when the density of data of the distances of points is made thin, there is a risk of overlooking of the distortion of a local portion between points.

In either method of measuring the optical distortion, a picture of the polka dots or the group of points is taken through the measured material while the imaging device such as the ITV camera or the like is moved. Therefore, error of measured distance is apt to occur due to mechanical vibrations caused when the imaging device is moved. Further, since a range of picture taken by the imaging device by once time is small, it is necessary to repeat a large number of times of movement and treatments for picture. Accordingly, it takes much time for the process.

When the imaging device is used, there occasionally causes blooming or out of focusing. Therefore, error of dimensions of the diameters in the longitudinal and lateral directions of the polka dots becomes large. Further, error of the position of dispersed bright point coordinates of the group of points becomes large. As a result, accuracy of measuring of the optical distortion will decrease.

SUMMARY OF THE INVENTION

It is an object of the present invention to provide a method of and an apparatus for measuring optical distortion which correctly measures the optical distortion of a measured material while influence of out of focusing is minimized; simplifies treatments for measuring, and facilitates a wide range of measurement.

In an aspect of the present invention, there is provided a method of measuring optical distortion of measured material by disposing a background screen (2) having a predetermined regular pattern (3) in rear of a measured material (1) having light transmission properties; disposing an image pick-up device (4) capable of line-scanning in front of the measured material (1); taking a picture of the background screen through the measured material (1) by successively line-scanning the entirety of a range to be measured of the measured material (1) with the image pick-up device (4), and measuring the optical distortion of the measured material (1) on the basis of data in the picture, the method being characterized in that the regular pattern (3) of the background screen is composed of triangle-wave-like unit patterns (3a), each extending continuously in a predetermined direction, which are arranged at distances of equal pitch.

In another aspect of the present invention, there is provided an apparatus for measuring optical distortion of measured material which comprises:

a background screen (2) disposed in rear of a measured material (1) having light transmission properties, and having a regular pattern (3) composed of triangle-wave-like unit patterns (3a) each extending continuously in a predetermined direction, which are arranged at distances of equal pitch, an image pick-up device (4) capable of line-scanning which is disposed in front of the measured material (1), a measurement range control means (5) to move at least one of the measured material (1), the image pick-up device (4) and the background screen (2) and to take a picture of the background screen (2) through the measured material (1) by successive line-scanning the entirety of a range to be measured of the measured material (1) with the image pick-up device (4), a pattern change point detection means (6) to detect change points of the regular pattern (3) of the background screen (2) by the line-scanning of the image pick-up device (4), a pattern segment extracting means (7) to extract pattern segments of the triangle-wave-like unit patterns (3a) on the basis of the pattern change points detected by the pattern change point detection means (6), a characteristic point operating means (8) to operate characteristic points from the pattern segments extracted by the pattern segment extracting means (7), a reference characteristic point storing means (9) to previously store coordinates of characteristic point obtained by photographing the background screen without interposing the measured material (1), and a distortion evaluating means (10) to evaluate the optical distortion of the measured material (1) by comparing coordinates of characteristic point obtained by interposing the measured material operated by the characteristic point operating means (8) with the coordinates of characteristic point in the reference characteristic point storing means (9).

In the present invention, the background screen 2 may be such one that a light source for illumination is disposed in rear of a light transmitting screen material on which an opaque regular pattern 3 is drawn so that light passes through the screen material except for the regular pattern 3. Or, the background screen may be such that a light source for illumination is disposed in rear of an opaque screen material on which a light transmitting regular pattern 3 is drawn so that light passes through the regular pattern 3. Further, it may be such one that a regular pattern 3 is drawn on a screen material by using, for instance, emission coating, and light is irradiated to the regular pattern 3 from the outside. Thus, the above-mentioned or other various means may be suitably selected for the background screen 2.

The direction of arrangement of the regular pattern 3 can be selected to have a previously determined optional direction. It is however preferable to arrange it in the longitudinal direction or a lateral direction in consideration of easiness of treatment.

The shape of each of the triangle-wave-like unit patterns 3a as the regular pattern 3 can be determined to have any relation of θ1=θ2, θ1>θ2 or θ1<θ2 wherein θ1 and θ2 designate slanting angles of sides of the triangle-wave-like unit patterns 3a with respect to a reference line (which extends in the direction perpendicular to the direction of arrangement of the regular pattern 3). In considering easiness of treatment, a relation of θ1=θ2 is preferred. However, when the slating angles θ1 and θ2 of the triangle-wave-like unit patterns 3a are too small, there is a case that the slanting line portions of the triangle-wave-like unit patterns can not be recognized due to a distortion of the slanting line portions. Accordingly, the slanting angles should be in a range of about 45°±30°.

A pitch $P_1$ in the arrangement of the triangle-wave-like unit patterns 3a can be suitably selected as far as it can be recognized by the resolution of the image pick-up device 4. By setting a pitch P of the width of the triangle-wave-like unit patterns 3a to be substantially the same as the pitch $P_1$ between the arranged unit patterns 3a, the position of pattern change points (points in the vicinity of edges of the unit patterns 3a) in scanning operations is uniform, and accordingly, it is possible to easily distinguish the pattern change points from noise components.

The image pick-up device 4 may be selected suitably as far as it can take a picture of the background screen 2 through the measured material 1. An arrangement of pick-up elements for each pixel such as photosensors arranged in a matrix form or a CCD line sensor camera may be used for the image pick-up device 4, whereby the presence or absence of light received by each pixel can be easily detected, and treatment for data can be easy.

The direction of scanning of the image pick-up device 4 is also optional. Considering easiness of treatment, it is preferable that the direction of scanning of the image pick-up device 4 is along the direction of the arrangement of the triangle-wave-like unit patterns 3a (i.e., the direction perpendicular to the extending direction of the triangle-wave-like unit patterns 3a).

The measurement range control means 5 is required to take a picture in the entirety of a range to be measured of the measured material 1 with the image pick-up device 4, and to take a picture of the regular pattern on the background screen 2 through the measured material 1. For instance, it controls the range of measurement by moving (circularly or linearly) stepwise the measured material 1 or the image pick-up device 4, moving stepwise the image pick-up device 4 and the measured material 1, or moving stepwise the image pick-up device 4 and the background screen 2.

A pattern change point corresponds to a cross point for dark and bright.

The pattern change point detection means 6 may be of a suitable type as far as it can detect points in the vicinity of edges of the regular pattern 3 through which the scanning lines of the image pick-up device 4 traverse. It is preferable to utilize an edge detecting system which can detect correctly points in the vicinity of edges of the regular pattern 3 even when a picture image taken by the image pick-up device 4 is out of focus.

A pattern segment corresponds to a side of the triangle-wave-like unit patterns 3a. The pattern segment extracting means 7 for recognizing pattern segments can be selected from suitable devices as far as they can extract pattern segments from the locus of extracted pattern change points. In order to extract the pattern segments with high accuracy, the pattern segment extracting means 7 should be so adapted to obtain, for instance, a line of least square approximation on the basis of a train of pattern change points, or to remove noises from the train of pattern change points in consideration of features of the regular pattern 3 (e.g., an inclination angle, a pitch of width of pattern, a pitch between patterns).

The characteristic point operating means 8 can be selected from suitable devices as far as they can operate, from extracted pattern segments, characteristic points, for instance, intersections of pattern segments or intersections of center lines of parallel pattern segments, of the regular pattern.

A reference characteristic point (hereinbelow, referred to simply as a reference point) may be a characteristic point obtained by directly taking a picture of the background screen 2 without interposing the measured material 1, or a characteristic point obtained by measuring actually the measured material without having any optical distortion, or a characteristic point obtained by theoretically analyzing the regular pattern on the background screen 2. In this invention, the reference point is defined such that it is obtained without interposing the measured material 1.

The distortion evaluating means 10 may be so constructed that a distortion quantity is calculated by comparing characteristic points operated in the characteristic point operating means 8 with reference points, and numerical values of distortion quantity are displayed so that an operator can judge the magnitude of optical distortion, or the operator can judge whether or not the distortion quantity obtained by the calculation is within an acceptable level, i.e. a reference distortion quantity.

According to the above-mentioned techniques, the measurement range control means 5 moves at least one among the measured material 1, the image pick-up device 4 and the background screen 2 to take a picture of the regular pattern 3 in the background screen 2 through the measured material in the entirety of a range to be measured of the measured material 1.

The regular pattern 3 is composed of the triangle-wave-like unit patterns 3a which substantially extend continuously in a predetermined direction, for instance, the longitudinal direction and are arranged at distances of equal pitch $P_1$. Accordingly, when line-scanning is conducted by the image pick-up device 4, the pattern change point detection means 6 detects as a pattern change point an edge of a triangle-wave-like unit pattern 3a, which is traversed by a scanning line.

If a picture image taken by the image pick-up device 4 is out of focus during the detection of pattern change points, the pattern change points can be correctly detected by suitably setting a threshold value of the contrast of a transmitting light quantity. It is because a point having a fixed light quantity can be determined as a pattern change point by setting the threshold value of the contrast of a transmitting light quantity, and pattern change points must be on the edge of the triangle-wave-like unit patterns 3a having a constant pitch $P_1$ of arrangement.

The pattern segment extracting means 7 extracts pattern segments on the basis of pattern change points detected. In this case, it is expected that the pattern change points are arranged substantially along the inclination angle of each of the triangle-wave-like unit patterns 3a even when the optical distortion is more or less large, since the pattern change points must be arranged along the edge line of triangle-wave-like unit patterns 3a (the inclination angles θ1 and θ2 are previously determined primarily). Accordingly, the pattern segments can be extracted easily from a train of pattern change points.

Then, the characteristic point operating means 8 operates characteristic points such as intersections of pattern segments from the extracted pattern segments. Thus, the coordinate of the characteristic points operated by the distortion evaluating means 10 is compared with the coordinate of characteristic points stored in the reference point storing means 9 whereby the optical distortion of the measured material 1 is judged.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF PREFERRED EMBODIMENTS

Preferred embodiments of the present invention will be described in more detail with reference to the drawings.

Figure 1:
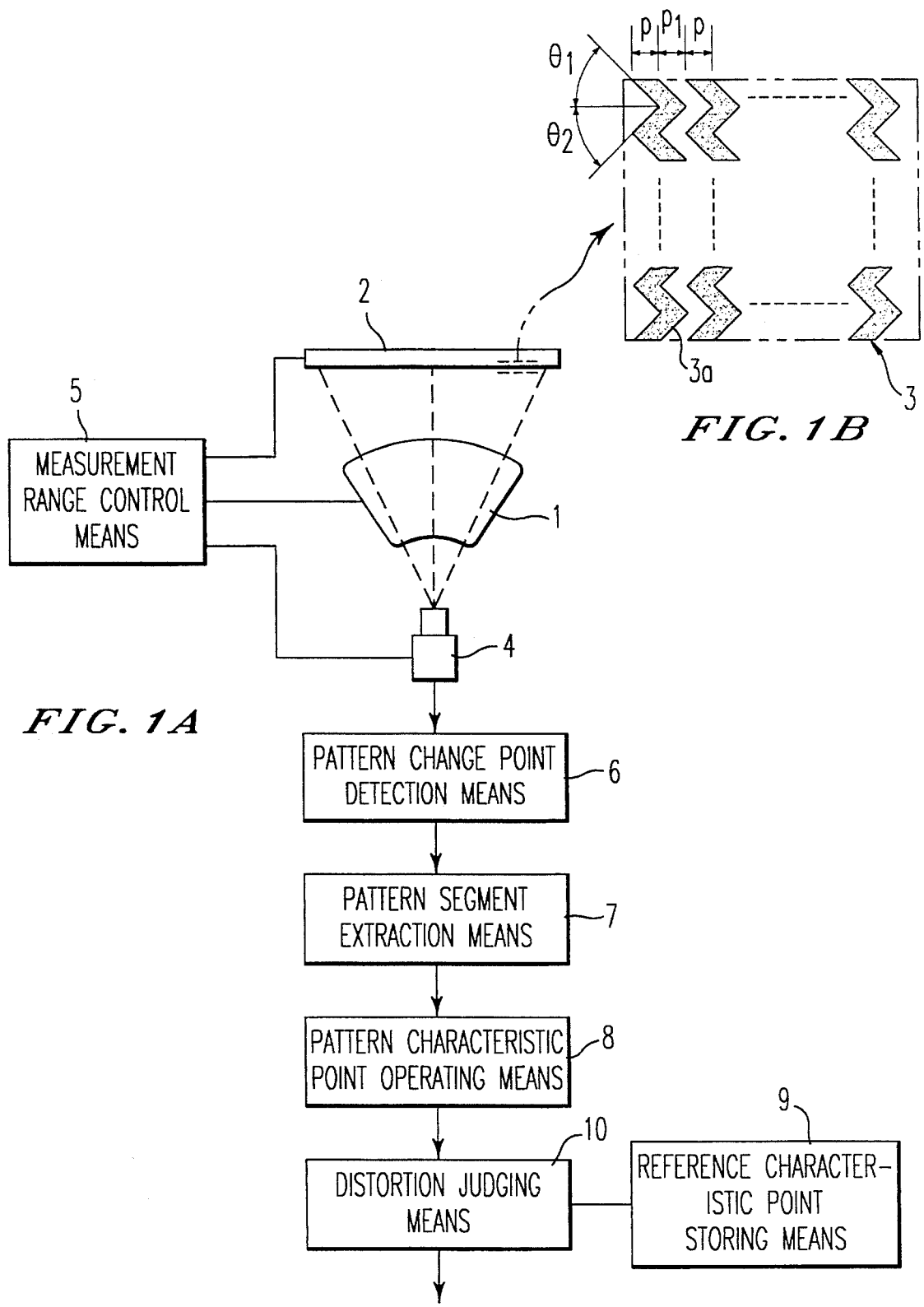
FIGS. 1A and 1B are a diagrams showing an embodiment of the method of and the apparatus for measuring optical distortion according to the present invention.
Figure 2:
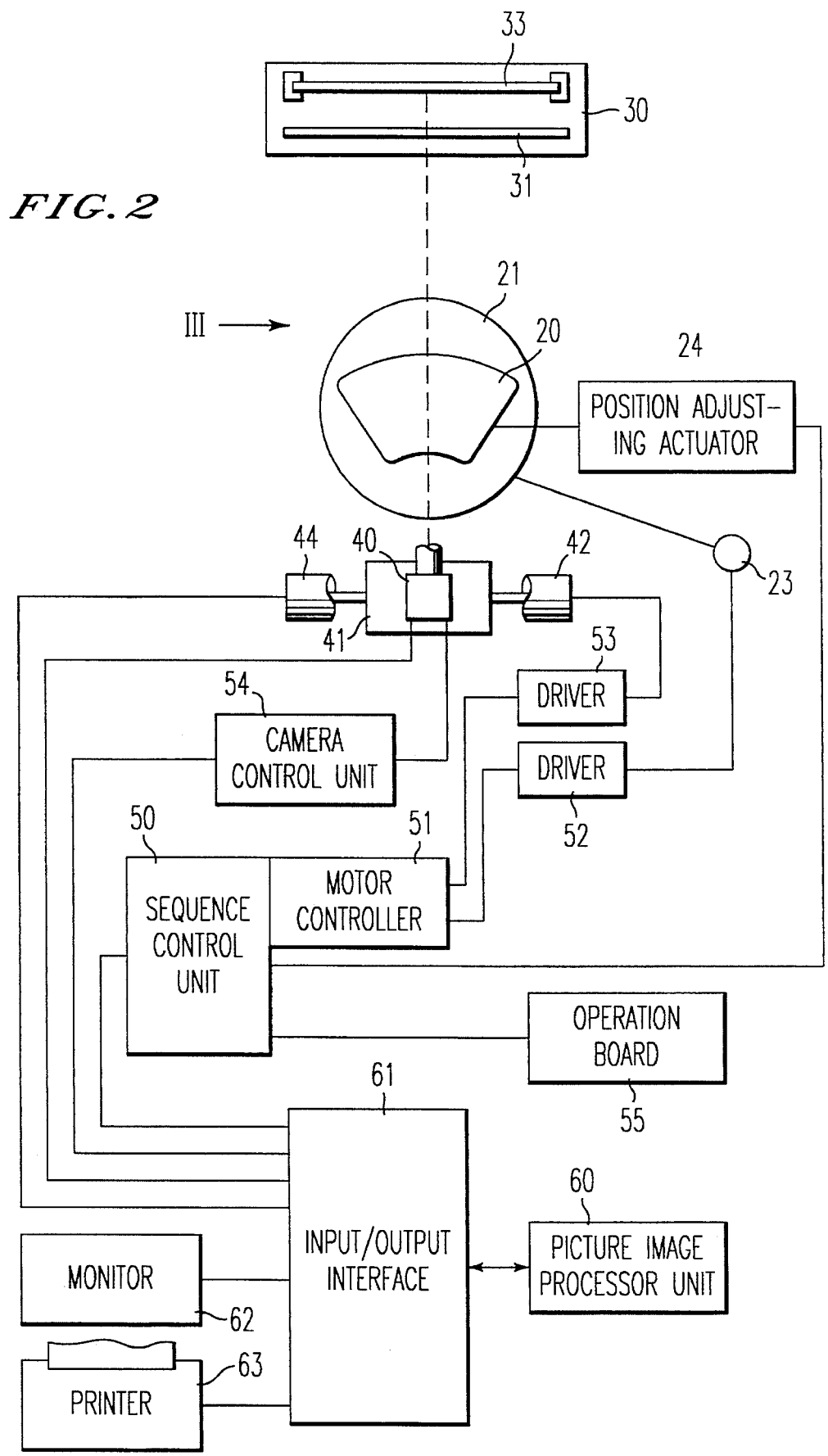
FIG. 2 is a diagram showing an embodiment of the apparatus for measuring optical distortion according to the present invention.
Figure 3:
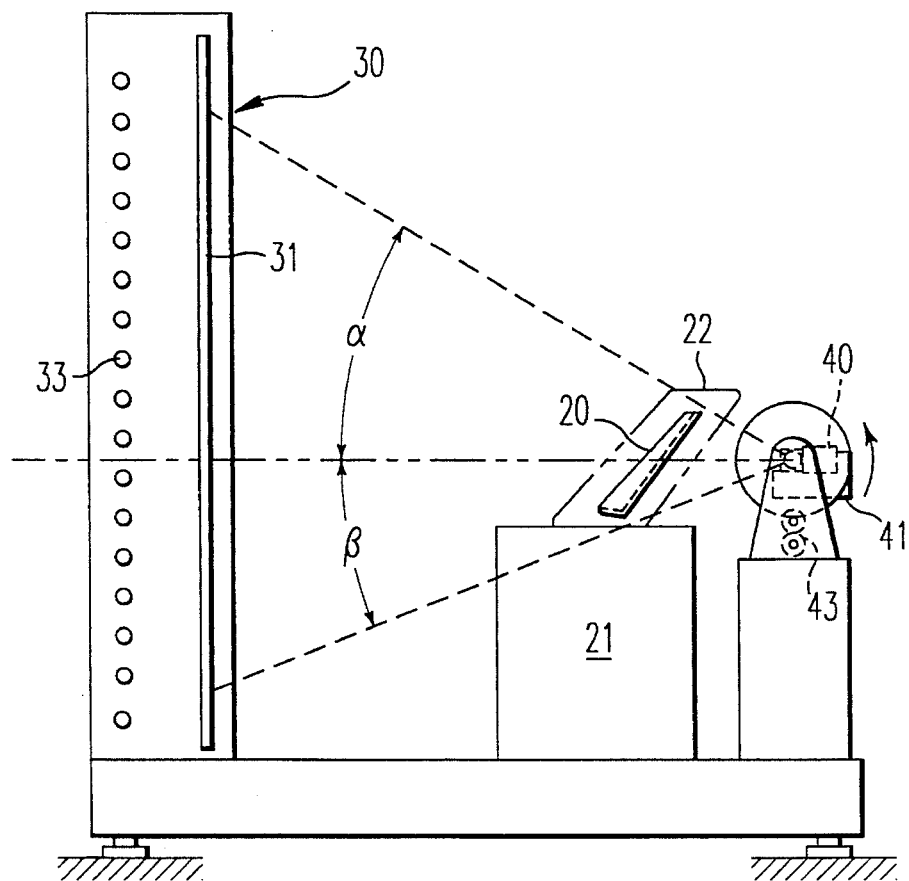
FIG. 3 is a diagram viewed from the direction of a mark III in FIG. 2.

FIGS. 2 and 3 show an embodiment of the apparatus for measuring optical distortion according to the present invention. In FIGS. 2 and 3, reference numeral 20 designates a work as a measured material (a front window glass sheet for an automobile in this embodiment). The work 20 is held in a predetermined posture of inclination on a rotatable work table 21 by means of a holder 22. Numeral 23 designates a table driving motor which turns the work table 21 within a predetermined angular range (e.g., about 160° in this embodiment) and numeral 24 designates a work position adjusting actuator which adjusts the position in the vertical direction and the angle of the work 20 by adjusting the position of the holder 22 on the work table 21.

A background screen 30 is disposed in rear of the work 20. The background screen 30 comprises a screen sheet 31 having light transmission properties in front of a screen frame (not shown) and a predetermined regular pattern 32 having non-transmission properties which is formed on the front surface of the screen sheet 31. A number of rod-like light sources 33 are arranged in the vertical direction with predetermined intervals at the rear side of the screen sheet 31 so that the screen sheet 31 is irradiated from the back side.

Figure 4:
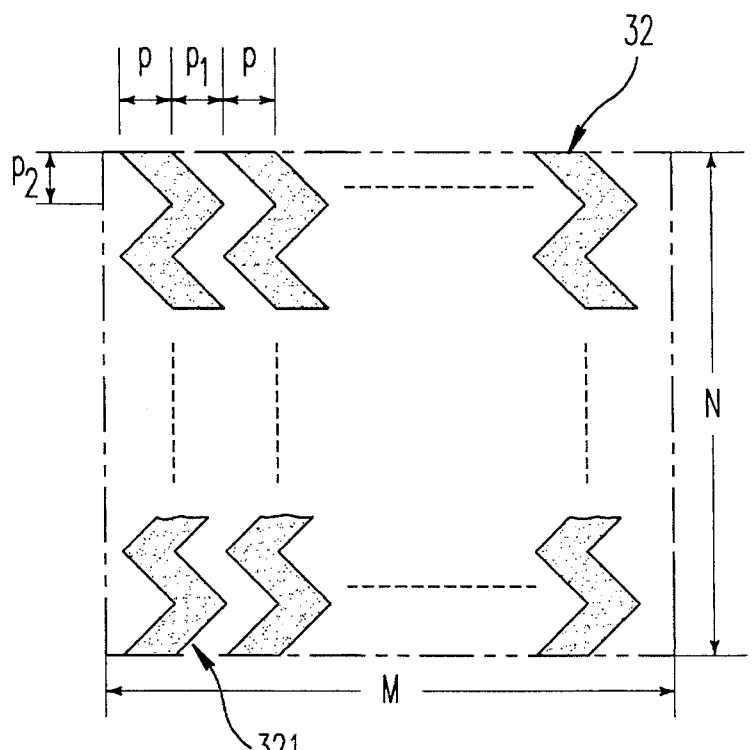
FIG. 4 is a diagram showing an embodiment of a regular pattern in a background screen.

In this embodiment, as shown in FIG. 4 in particular, the regular pattern 32 comprises a number of triangle-wave-like unit patterns 321, each extending in the longitudinal direction, which are arranged in the lateral direction with distances of predetermined pitch $P_1$ (e.g., 7.5 mm in this embodiment). The triangle-wave-like unit patterns 321 are formed over a range of M×N (e.g., 780×3420 mm in this embodiment). Each of the triangle-wave-like unit patterns 321 has a pitch P of width (e.g., 7.5 mm in this embodiment) and a bent portion with a pitch $P_2$ (e.g., 7.5 mm in this embodiment) in the longitudinal direction at an angle of inclination of 45° with respect to a reference line which is a horizontal line.

Numeral 40 designates a CCD line sensor camera (hereinbelow, referred to simply as a CCD camera in this embodiment) which is disposed in front of the work 20. In this embodiment, 4096 CCDs are used as pick-up elements which are driven by a two phase driving system (wherein a group of CCDs belonging to an odd number and a group of CCDs belonging to an even number are driven in different two phases).

The distance between the CCD camera 40 and the screen sheet 31 of the background screen 30 is determined to be about 3 m in this embodiment.

The CCD camera 40 is fixed onto a movable support bracket 41 which is rotatable around a horizontal axis. The posture of the CCD camera 40 in a state of inclination can be changed by transmitting a rotary motion of a servo motor 42 to the support bracket 41 through a transmission gear 43. In this embodiment, an elevation angle α and a depression angle β of the camera 40 are determined to be in a range from ±30° to −25°.

Numeral 44 designates a rotary encoder attached to the rotary shaft of the support bracket 41 to detect the posture angle of the CCD camera 40.

Numeral 50 designates a sequence control unit for automatically controlling a series of image pick-up treatments by the CCD camera 40. The sequence control unit 50 produces motor driving signals from a motor controller 51; controls the movement of the table driving motor 23 and the servo motor 42 for rotating camera by means of drivers 52, 53, and controls the image pick-up treatments of the CCD camera 40 by means of a camera driving unit 54.

When processing sequence of the sequence control unit 50 is to be set or changed, an operator can provide a direct instruction through an operating board 55, or an instruction signal can be given from an image processing control unit 60 which is connected to the CCD camera 40, the rotary encoder 44 and the sequence control unit 50 through an input-output interface 61. The control unit 60 is capable of treating the picture data by the CCD camera 40; obtaining various kinds of information such as the optical distortion of the work 20, and outputting the information to a monitor 62 and a printer 63.

In the following, the input-output interface 60 used in this embodiment will be described in detail.

Figure 5:
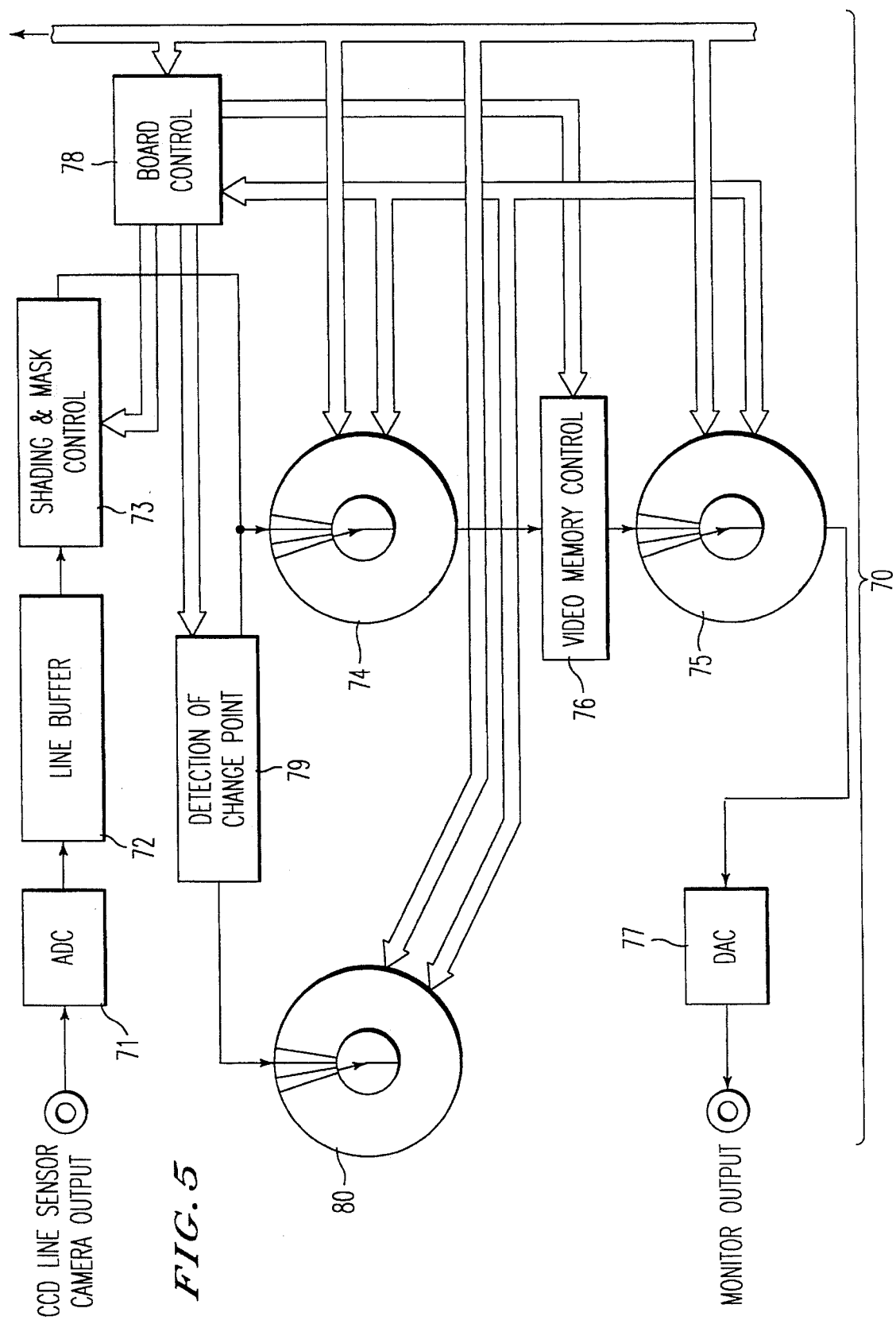
FIG. 5 is a diagram showing an embodiment of a sensor interface board used for the present invention.

FIG. 5 is a diagram showing an embodiment of the contraction of a sensor interface board 70 in the input-output interface 61 to receive a signal from the CCD camera 40.

Figure 6:
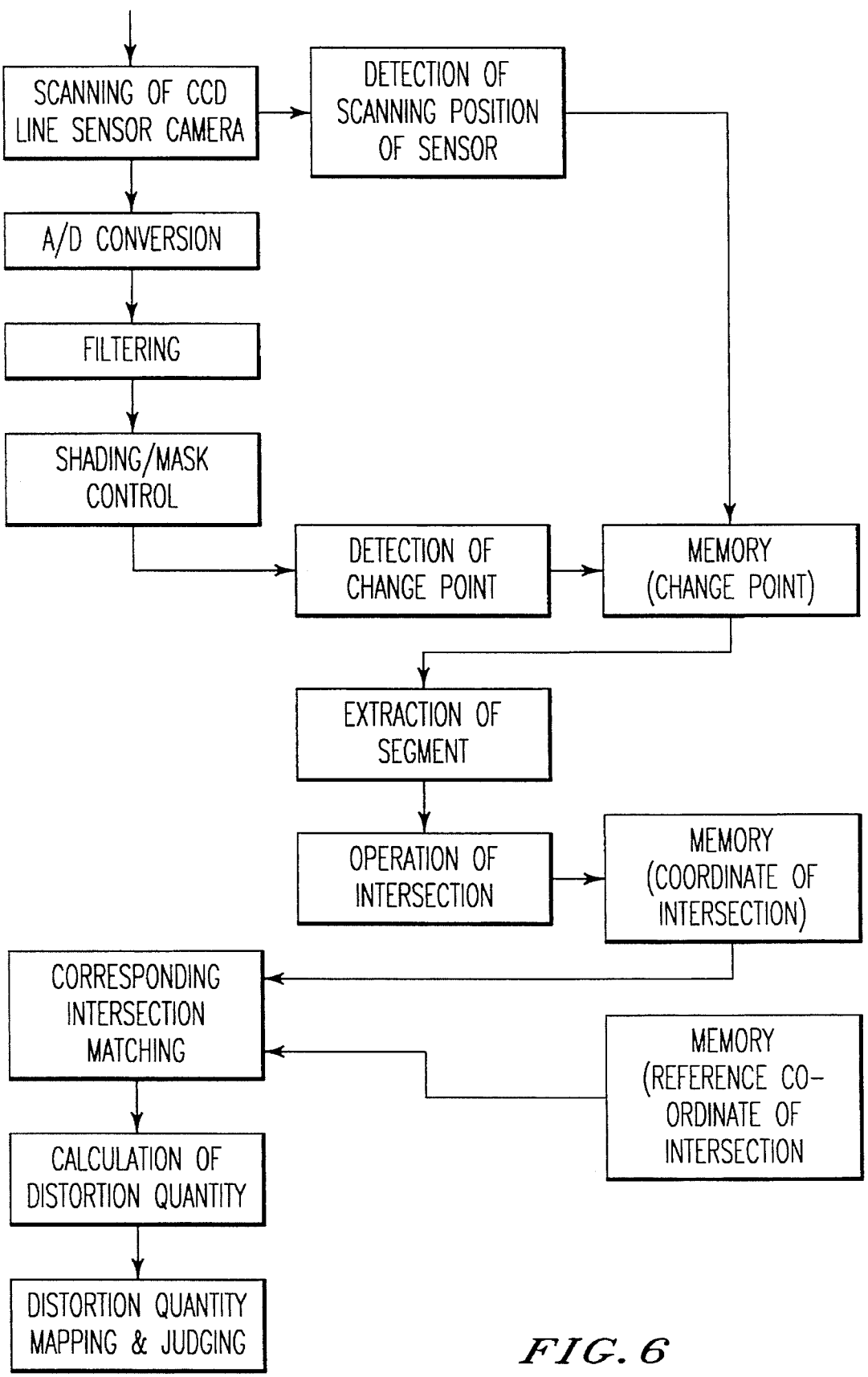
FIG. 6 is a flow chart showing the steps of measuring optical distortion according to the present invention.

In FIG. 6, reference numeral 71 designates an analogue-digital converter to convert input analogue signals into digital data; numeral 72 a FIFO line buffer for successively storing digital data for one line scanning by the CCD camera 40; numeral 73 a data correction circuit for effecting shading and masking to the digital data obtained; numeral 74 a ring-shaped frame memory for storing temporarily the digital data which have been corrected in the data correction circuit 73; numeral 75 a ring-shaped frame memory (video memory) storing temporarily digital image signals for outputting; numeral 76 a video memory control circuit for controlling addressing operations by the video memory 75; numeral 77 a digital-analogue converter for converting the digital image signals read by the video memory 75 into analogue signals; numeral 78 a board control section in which programs for controlling the sensor interface board 70 are stored; numeral 79 a change point detection portion for detecting pattern change points; and numeral 80 a ring buffer memory for storing the pattern change points detected by the change point detection portion.

Further, in this embodiment, the analogue-digital converter 71 is so adapted to average a difference of alternating sensitivity of the CCDs belonging to the groups of odd number and even number, which is resulted from the two phase driving system of the CCD camera 40 to thereby remove noises caused by the difference of alternating sensitivity of the CCDs, in addition to the fundamental function of converting analogue signals into digital data.

A treating process by the apparatus for measuring optical distortion of this embodiment will be described.

The CCD camera 40 and the work 20 are stepwisely rotated by signals from the sequence control unit 50, and the CCD camera 40 takes a picture of the regular pattern 32 in the background screen 30 through the work 20 over the entirety of a range of the work 20.

Figure 7A:
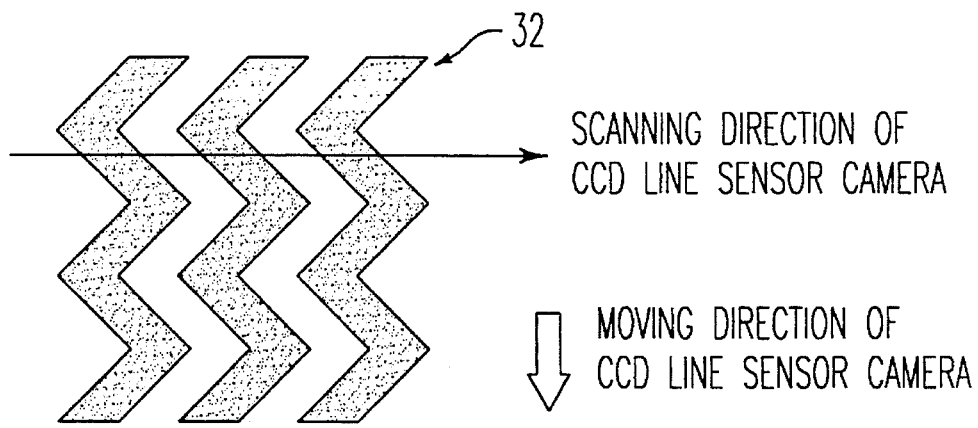
FIG. 7a is a diagram showing the relation between the regular pattern and a scanning line by a CCD line sensor camera.

In FIG. 6, analogue signals from the CCD camera 40 are taken for each scanning line of the CCD camera 40, the analogue signals are subjected to A-D conversion. Then, the digital signals are filtered, and the filtered signals are subjected to shading correction and mask control. Thus, the obtained digital data are once stored in the frame memory 74. In parallel to this, the pattern change points are detected in the change point detection portion 79. FIG. 7 shows as a model treatments of detection of the pattern change points. As shown in FIG. 7a, pitches of transmission/non-transmission patterns (regular patterns 32) during line-scanning of the CCD camera 40 are equal and uniform. This relation can be always kept even when a position of scanning by the CCD camera 40 is moved in the sub-scanning direction as shown by an arrow mark.

Figure 7B:
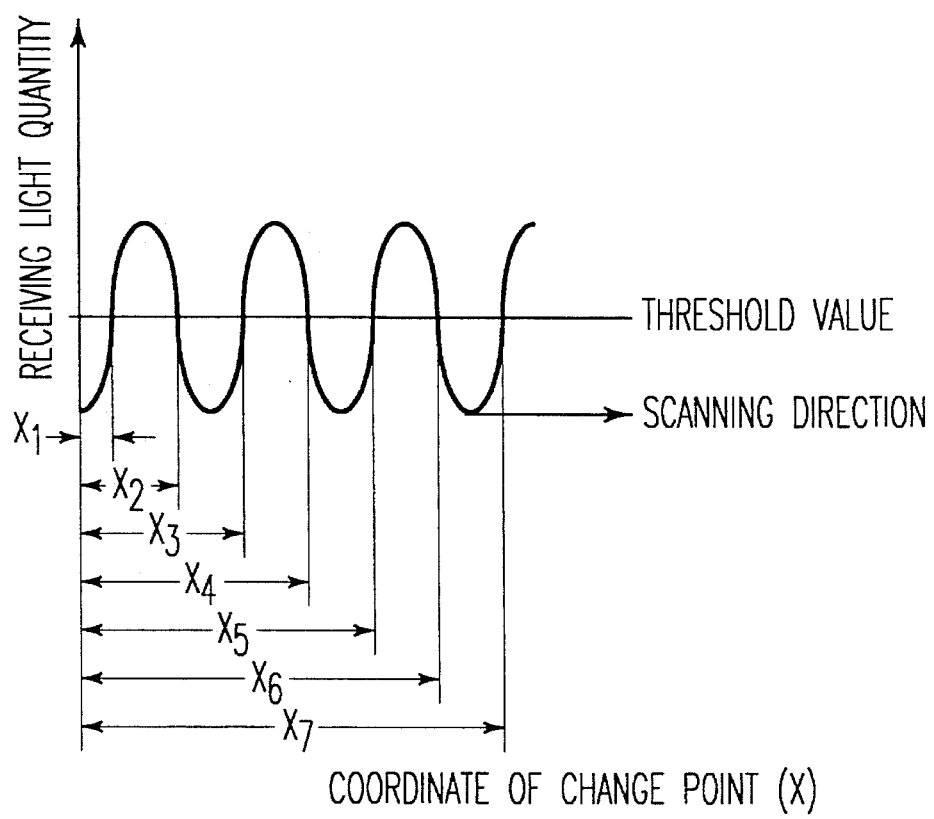
FIG. 7b is a diagram for illustrating detection of pattern change points.

As described before, there is a case that an image taken by the CCD camera 40 is out of focus. However, as described above, the transmission—non-transmission patterns are at equal pitches. Accordingly, as shown in FIG. 7b, by determining as a threshold value a level of 50% to the contrast of a received light quantity, defocusing at a point in the vicinity of an edge line between the transmission and non-transmission patterns can be canceled. Thus, pattern change points (edge) ($x=x_1-x_7$ in FIG. 7b) can be correctly detected, and the pattern change points are successively stored in the ring buffer memory 80.

Then, a main CPU (or a signal processor) successively reads out the coordinate data of the pattern change points from the ring buffer memory (change point storing memory) 80 to conduct an extraction treatment of pattern segments.

In this case, coordinates of pattern change points must be aligned along the edge line of the triangle-wave-like unit pattern 321. Accordingly, even though the work 20 has optical distortion, the coordinates of pattern change points must be recognized continuously with an inclination of about 45° with respect to a horizontal line as the reference line. Noise components are removed from the detected pattern change points. Then, an expression of pattern segment is given by obtaining a line of least square approximation on the basis of a train of the coordinates of pattern change point.

Then, the coordinate of intersection of continuous pattern segments is obtained as the coordinate of characteristic point from the expression of line obtained as described above. In this case, a point at which pattern segments intersects at a substantially right angle can be calculated as the intersection. Intersections of lines other than the pattern segments can be removed in calculation operations whereby only required coordinates of intersection are obtainable.

Figure 8A:
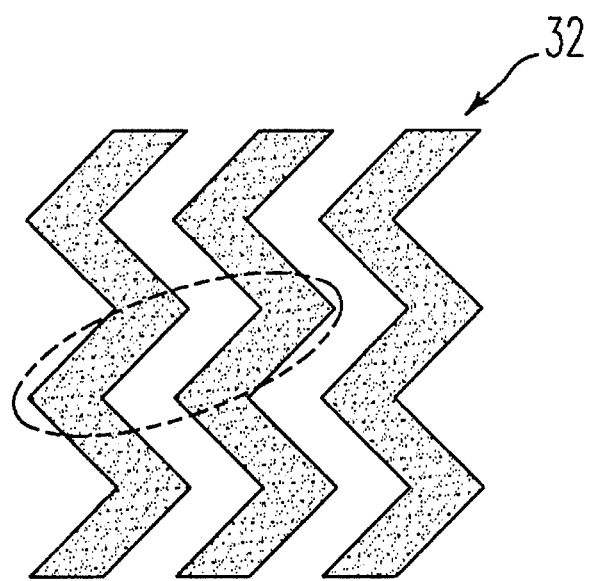
FIG. 8a is a diagram showing an example of picture data in which there is distortion in a work.

Then, the main CPU (or signal processor) conducts a distortion evaluating treatment on the basis of the coordinates of intersection. Assuming that there is distortion in a tested work 20. For instance, there is distortion in an image of the regular pattern 32 obtained by taking a picture with use of the CCD camera 40 as indicated by a circular broken line in FIG. 8a. In this case, there is irregularity of pitches in the positions of pattern change point. This influences the inclination angle of pattern segments to be extracted and reflects the coordinates of intersection to be extracted.

In this embodiment, coordinates of intersection obtained by taking a picture of the background screen 30 without interposing the work, namely, coordinates of intersection in a state that the work has no distortion are stored as reference data in, for instance, a disk memory. Then, data of the coordinates of intersection obtained by actually measuring the work 20 are compared for matching treatment with data of the reference coordinates of intersection. By conducting calculating operations described below, a distortion quantity is obtained to thereby evaluate the distortion quantity of the work 20.

Figure 8B:
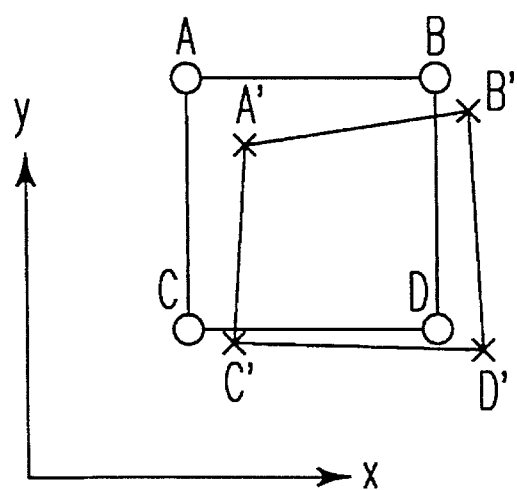
FIG. 8b is a diagram showing a treatment of calculating a distortion quantity.

In FIG. 8*b*, characters A, B, C and D represent data of the reference coordinate of intersection, and A', B', C' and D' represent data of actually measured coordinates of intersection.

When a vector CD is represented as CD($\rightarrow$); the inner product of CD($\rightarrow$) and C'D'($\rightarrow$) is represented as <CD($\rightarrow$)*C'D'($\rightarrow$)>, and the length of CD($\rightarrow$) is represented as |CD($\rightarrow$)|, the angle $\theta_H$ formed between CD($\rightarrow$) and C'D'($\rightarrow$) is obtained as:

$$\theta_H = \cos^{-1}\{<CD(\rightarrow)*C'D'(\rightarrow)>/(|CD(\rightarrow)|*|C'D'(\rightarrow)|)\}.$$

Similarly, the angle $\theta_V$ formed between CA($\rightarrow$) and C'A'($\rightarrow$) is obtained as:

$$\theta_V = \cos^{-1}\{<CA(\rightarrow)*C'A'(\rightarrow)>/(|CA(\rightarrow)|*|C'A'(\rightarrow)|)\}.$$

Thus, a distortion quantity $\theta$ at the point C can be evaluated by the average value of these two angles, i.e. $\theta = \alpha\theta_H + (1-\alpha)\theta_V$ ($\alpha$ is a weighting coefficient). In this case, when $\alpha < 0.5$, there is obtainable a distortion quantity in which the distortion in the longitudinal direction is considered to be more important than the distortion in the lateral direction. When it is unnecessary to weight between the longitudinal direction and the lateral direction, $\alpha = 0.5$ is satisfactory.

Thus, the distortion quantity of each intersection is calculated. Then, the calculated distortion quantities are evaluated as to whether or not these are within a predetermined acceptable level, and the result of evaluation is outputted to the monitor 62 in a form of distortion quantity mapping display.

As described above, the apparatus for measuring optical distortion according to this embodiment is capable of real-time processing of signals from the CCD camera 40 until the time of detecting the pattern change points. Further, high speed processing can be realized with use of the main CPU (or a signal processor) because density of data is high.

Further, since the CCD camera 40 is used in this embodiment, a horizontal resolution of about 8 times as that by a conventional ITV camera (about 1/500) can be obtained. Accordingly, high speed processing and highly accurate measuring are possible in spite of simple processing in comparison with a technique that the diameters in the longitudinal and lateral directions of polka dots are detected.

Further, in the present invention, since a distortion quantity can be calculated on the basis of irregularity of continuously arranged triangle-wave-like unit patterns, it is possible to measure effectively distortion in a narrow thin region in comparison with the technique wherein a regular pattern composed of trains of points is used, and a distortion quantity is calculated on the basis of a change of the coordinate of dispersed bright points of the trains of points.

As described above, in accordance with the present invention wherein an image pick-up device takes a picture of a regular pattern in a background screen through a measured material, optical distortion can be correctly measured while influence by defocusing of the image pick-up device is minimized by improving the regular pattern in the background screen. Further, measuring treatment can be simplified and a wide range of measurement is possible. Particularly, in accordance with the apparatus of the present invention, the above-mentioned requirements can be realized easily and certainly.

In addition, use of triangle-wave-like patterns as the regular pattern is effective to measure the optical distortion of a glass sheet for an automobile. There is a case that the glass sheet for an automobile is provided with a ceramic print such as a black color at its peripheral portion. When the ceramic print is overlapped with the regular pattern in the background screen, error of detecting pattern change points may take place. However, use of the triangle-wave-like unit patterns of the present invention facilitates removing as irregular data the detection data of the ceramic print at the peripheral portion of the glass sheet. Namely, when there is a large difference between the detected data and data to be detected, the detected data can be removed from data for evaluating distortion. When the ceramic print portion is detected, the detected data correspond to a pattern along the shape of the peripheral portion of the glass sheet. Accordingly, the detected data is clearly distinguishable from the pattern detection data. Further, the triangle-wave-like unit pattern is desirable as a pattern capable of correctly recognizing pattern change points.

The removal of unnecessary data improves accuracy of quantifying the distortion quantity. Further, since the data portion to be removed is at the peripheral portion of the glass sheet, it is possible to extract the contour of the glass sheet (measured material).

Obviously, numerous modifications and variations of the present invention are possible in light of the above teachings. It is therefore to be understood that within the scope of the appended claims, the invention may be practiced otherwise than as specifically described herein.

What is claimed is:

1. A method of measuring optical distortion of measured material by disposing a background screen (2) having a predetermined regular pattern (3) in rear of a measured material (1) having light transmission properties; disposing an image pick-up device (4) capable of line-scanning in front of the measured material (1); taking a picture of the background screen through the measured material (1) by successively line-scanning the entirety of a range to be measured of the measured material (1) with the image pick-up device (4), and measuring the optical distortion of the measured material (1) on the basis of data in the picture, the method being characterized in that the regular pattern (3) of the background screen is composed of triangle-wave-like unit patterns (3*a*), each substantially extending continuously in a predetermined direction, which are arranged at distances of equal pitch.

2. The method of measuring optical distortion according to claim 1, wherein the width of each of the triangle-wave-like unit patterns (3*a*) is equal to the distances of pitch of the same.

3. The method of measuring optical distortion according to claim 1, wherein the measured material is a glass sheet for an automobile.

4. An apparatus for measuring optical distortion of measured material which comprises:

a background screen (2) disposed in rear of a measured material (1) having light transmission properties, and having a regular pattern (3) composed of triangle-wave-like unit patterns (3*a*) each extending continuously in a predetermined direction, which are arranged at distances of equal pitch, an image pick-up device (4) capable of line-scanning which is disposed in front of the measured material (1), a measurement range control means (5) to move at least one of the measured material (1), the image pick-up device (4) and the background screen (2) and to take a picture of the background screen (2) through the measured material (1) by successively line-scanning the entirety of a range to be measured of the measured material (1) with the image pick-up device (4), a pattern change point detection means (6) to detect change points of the regular pattern (3) of the background screen (2) by the line-scanning of the image pick-up device (4), a pattern segment extracting means (7) to extract pattern segments of the triangle-wave-like unit patterns (3a) on the basis of the pattern change points detected by the pattern change point detection means (6), a characteristic point operating means (8) to operate characteristic points from the pattern segments extracted by the pattern segment extracting means (7), a reference characteristic point storing means (9) to previously store coordinates of characteristic point obtained by photographing the background screen without interposing the measured material (1), and a distortion evaluating means (10) to evaluate the optical distortion of the measured material (1) by comparing coordinates of characteristic point obtained by interposing the measured material operated by the characteristic point operating means (8) with the coordinates of characteristic point in the reference characteristic point storing means (9).

5. The apparatus for measuring optical distortion according to claim 4, wherein the width of the triangle-wave-like unit patterns (3a) is equal to the distances of pitch of the same.

6. The apparatus for measuring optical distortion according to claim 4, wherein the measured material is a glass sheet for an automobile.

* * * * *